(12) United States Patent
Luthringer et al.

(10) Patent No.: US 9,732,059 B2
(45) Date of Patent: Aug. 15, 2017

(54) METHODS OF USE OF CYCLIC AMIDE DERIVATIVES TO TREAT SCHIZOPHRENIA

(75) Inventors: Remy Henri Luthringer, Geneva (CH); Lorenzo Pellegrini, Newtown, PA (US); Argeris N. Karabelas, Portsmouth, NH (US)

(73) Assignee: Minerva Neurosciences, Inc., Waltham, MA (US)

( * ) Notice: Subject to any disclaimer, the term of this patent is extended or adjusted under 35 U.S.C. 154(b) by 547 days.

(21) Appl. No.: 13/810,772

(22) PCT Filed: Jul. 20, 2011

(86) PCT No.: PCT/US2011/044697
§ 371 (c)(1),
(2), (4) Date: Jun. 24, 2013

(87) PCT Pub. No.: WO2012/012542
PCT Pub. Date: Jan. 26, 2012

(65) Prior Publication Data
US 2013/0274289 A1    Oct. 17, 2013

Related U.S. Application Data

(60) Provisional application No. 61/366,075, filed on Jul. 20, 2010.

(51) Int. Cl.
| | | |
|---|---|---|
| *A01N 43/40* | (2006.01) |
| *A61K 31/445* | (2006.01) |
| *C07D 401/06* | (2006.01) |
| *H04L 5/00* | (2006.01) |
| *H04W 4/00* | (2009.01) |

(52) U.S. Cl.
CPC .......... *C07D 401/06* (2013.01); *H04L 5/001* (2013.01); *H04L 5/005* (2013.01); *H04L 5/0016* (2013.01); *H04L 5/0019* (2013.01); *H04L 5/0048* (2013.01); *H04L 5/0053* (2013.01); *H04W 4/00* (2013.01)

(58) Field of Classification Search
None
See application file for complete search history.

(56) References Cited

U.S. PATENT DOCUMENTS

| 7,166,617 B2 | 1/2007 | Yamabe et al. |
| 2003/0212094 A1* | 11/2003 | Yamabe .............. C07D 401/06 514/300 |
| 2010/0029726 A1 | 2/2010 | Blackaby et al. |
| 2013/0274290 A1 | 10/2013 | Luthringer et al. |

FOREIGN PATENT DOCUMENTS

WO    WO 01/64670 A1    9/2001

OTHER PUBLICATIONS

Modell et al. (Pharmacopsychiatry, 1996, 29, 63-66).*
Kay (Schizophr Bull, 1987, 13, 261-276).*
International Search Report issued in International Application No. PCT/US11/44697.
Dutheil et al. Xenobiotic metabolozing enzymes in the central nervous system: Contribution of cytochrome P450 enzymes in normal and pathological human brian. Biochimie vol. 90, issue 3, Mar. 2008, pp. 426-436. p. 433. col. 1.
Kropp et al. Cytochrome P-450 2D6 and 2C19 polymorphisms and length of hospitalization in psychiatry. Clinical Laboratory [2006, 52(5-6):237-40] Abstract.
Marder et al. Aripiprazole in the treatment of schizophrenia: safety and tolerability in short-term, placebo-controlled trials. Schizophrenia Research vol. 61, Issues 2-3, Jun. 1, 2003, pp. 123-136 Abstract.
Yang et al. Clinical significance of sleep EEG abnormalities in chronic schizophrenia. Schizophrenia Research 82 (2006) 251-260 Abstract.
E.g., J. M. Walker et al., Pharmacological Reviews, 42:355-402, 1990.
H. H. Garza et al., J. Immunol., 151:4672-4680, 1993.
M. Dumont and S. Lemaire, Eur. J. Pharmacol., 209:245, 248, 1991.
D. W. Bonhaus et al., J. Pharmacol. Exp. Ther., 267:961-970, 1993.
D. C. Mash and C. P. Zabetian, Synapse, 12:195-205, 1992.
L. T. Meltzer et al., Neuropharmacology, 31:961-967, 1992.
J. C. Jaen.et al., J. Med. Chem., 36:3929-3936, 1993.
R. Quirion et al., TiPS, 13:85-86, 1992.
Bishara et al. "Upcoming Agents for the Treatment of Schizophrenia Mechanism of Action, Efficacy and Tolerability," Drugs, vol. 68, No. 16, p. 2269-2292, 2008.
Bonhaus D. et al., "[3H]BIMU-1 , a 5-Hydroxytryptamine3 Receptor Ligand in NG-108 Cells, Selectively Labels *Sigma-2* Binding Sites in Guinea Pig Hippocampus", The Journal of Pharmacology and Experimental Therapeutics, vol. 267, No. 2, p. 961-970, 1993.
Dumont M. et al. "Interaction of 1,3-di ( 2-[5-3 H] tolyl) guanidine with $\sigma_2$ binding sites in rat heart membrane preparations", European Journal of Pharmacology, vol. 209, p. 245-248, 1991.
Garza H. et al., "Characterization of a (+)-Azidophenazocine-Sensitive Sigma Receptor on Splenic Lymphocytes", The Journal of Immunology, vol. 151, p. 4672-4680, 1993.
Jaen J. et al., "Evaluation of the Effects of the Enantiomers of Reduced Haloperidol, Azaperol, and Related 4-Amino-1-arylbutanols on Dopamine and σ Receptors", J. Med. Chern., vol. 36, p. 3929-3936, 1993.
Jeste "Schizoaffective Disorder," National Alliance on Mental Illness, http://www.nami.org/Template.cfm?Section=By_Illness&Template=/ContentManagement!ContentDisplay.cfm&ContentiD=23043 Wayback Internet Archive, (Nov. 7, 2008).
Marder et al. "Aripiprazole in the treatment of schizophrenia: safety and tolerability in short-term, placebo-controlled trials", Schizophrenia Research, vol. 61, pp. 123-136, 2003.
Mash et al., "Sigma Receptors Are Associated With Cortical Limbic Areas in the Primate Brain", Synapse, vol. 12, p. 195-205, 1992.
Meltzer et al., "Lack of Involvement if Haloperidol-Sensitive Sigma Binding Sites in Modulation of Dopamine Activity and Induction of Dystonias by Antipsychotic Drugs", Neuropharmacology, vol. 31, No. 9, p. 961-967, 1992.

(Continued)

*Primary Examiner* — Dennis Heyer
*Assistant Examiner* — Daniel M Podgorski
(74) *Attorney, Agent, or Firm* — Cooley LLP; Heidi A. Erlacher; Thomas J. Paxton

(57) ABSTRACT

Disclosed herein are compositions and methods for treating schizophrenia and symptoms of schizophrenia, including negative symptoms of schizophrenia.

25 Claims, No Drawings

(56) References Cited

OTHER PUBLICATIONS

Quirion et al., "A proposal for the classification of sigma binding sites", TiPS, vol. 13, p. 85-86, Mar. 1992.
Walker J. M. et al., "Sigma Receptors: Biology and Function", Pharmacological Reviews, vol. 42, No. 4, p. 355-402, 1990.
Arnt, J. et al. "Do Novel Antipsychotics Have Similar Pharmacological Characteristics? A Review of the Evidence", Neuropsychopharmacology, 1998, vol. 18, No. 2, p. 63-101.
Buchanan et al. "Positive and Negative Symptom Response to Clozapine in Schizophrenic Patients With and Without the Deficit Syndrome", American Journal of Psychiatry, 1998, vol. 155, p. 751-760.
Dutheil et al. "Xenobiotic metabolozing enzymes in the central nervous system: Contribution of cytochrome P450 enzymes in normal and pathological human brain", Biochimie, vol. 90, Issue 3, Mar. 2008, pp. 426-436.
Buchanan et al. "Olanzapine Treatment of Residual Positive and Negative Symptoms", American Journal of Psychiatry, 2005, vol. 162, p. 124-129.
Gilmore D. et al. *"Review of the Pharmacological and Clinical Profile of Rimcazole"*, CNS Drug Reviews, vol. 10, No. 1, pp. 1-22.
Hashimoto et al. "Sigma Receptor Ligands: Possible Application as Therapeutic Drugs and as Radiopharmaceuticals", Current Pharmaceutical Design, vol. 12, No. 30, Oct. 1, 2006, p. 3857-3876.
Hashimoto et al. "Interactions of erythro-ifenprodil, threo-ifenprodil, erythro-iodoifenprodil, and eliprodil with subtypes of *sigma*-receptors" European Journal of Pharmacology, 273 (1995), p. 307-310.
Jones C. et al. "Animal Models of Schizophrenia", British Journal of Pharmacology, 2011, vol. 164, p. 1162-1194.
Kay, "The Positive and Negative Syndrome Scale (PANSS) for Schizophrenia", Schizophrenia Bulletin, 1987, vol. 13, No. 2, pp. 261-276.
Kropp et al. "Cytochrome P-450 2D6 and 2C19 polymorphisms and length of hospitalization in psychiatry", Clinical Laboratory, 2006, 52(5-6), pp. 237-240. Abstract.
Maurice et al. "The attenuation of learning impairments induced after exposure to CO or trimethyltin in mice by sigma(sigma) receptor ligands involves both sigma 1 and sigma 2 sites", British Journal of Pharmacology, May 1999, 127(2), p. 335-42.
Modell S. et al. "Efficacy and Safety of an Opiate Sigma-Receptor Antagonist (SL 82.0715) in Schizophrenic Patients with Negative Symptoms: and Open Dose-Tange Study", Pharmacopsychiat., 1996, vol. 29, p. 63-66.
Schwarcz G. et al. "Open Label Evaluation of the Novel Antipsychotic Compound BW234U in Chronic Schizophrenics", Drug Development Research, 1985, vol. 5, p. 387-393.

SEC Form 8-K filed Jun. 6, 2016, Minerva Neurosciences. Inc.
"View of NCT00861796 on Mar. 12, 2009", ClinicalTrials.gov archive, Mar. 12, 2009 Retrieved from the Internet: URL:http://clinicaltrials.gov/archive/NCT00861796/2009_03_12.
Whittemore E. et al. "Antagonism of N-Methyl-D-Aspartate Receptors by s Site Ligands: Potency, Subtype-Selectivity and Mechanisms of Inhibition", The Journal of Pharmacology and Experimental Therapeutics, 1997, vol. 282, No. 1, p. 326-338.
Yang et al. "Clinical significance of sleep EEG abnormalities in chronic schizophrenia", Schizophrenia Research, 2006, vol. 82, pp. 251-260.
Zasshi, Nippon Yakurigaku, Folia Pharmacologica Japonica, 1999, vol. 114, p. 12-23.
Summary of $3^{rd}$ Quarter Financial Results for year ended Mar. 31, 2010 (Unaudited); Mitsubishi Tanabe Pharma Corporation; Jan. 28, 2010, available on http://www.mt-pharma.co.jp/.
Davidson, M. et al., "MIN-101: A sigma2 and 5HT2 antagonist drug in development for the treatment of symptomatically stable schizophrenia patients with negative symptoms", Oral Presentation at the 55th Annual Meeting of the American College of Neuropsychopharmacology, Dec. 4-8, 2016 in Hollywood, Florida, available on goo.gl/xF5rdR.
Davidson, M. et al., "MIN-101: A Drug in Development for the Treatment of Negative Symptoms in Schizophrenia", Poster presentation at the 55th Annual Meeting of the American College of Neuropsychopharmacology, held Dec. 4-8, 2016 in Hollywood, Florida, available on goo.gl/MIR7Tn.
Luthringer, R., "Comparison of Three Sigma2 Ligands on Negative and Positive Symptoms of Schizophrenia", Exhibit C to Supplemental Declaration or Remy Luthringer Under 37 C.F.R. 1.132, Jan. 17, 2017.
Buckley, P.F., et al. "Pharmacological treatment of negative symptoms of schizophrenia: therapeutic opportunity or Cul-de-sac?", Acta Psychiatrica Scandinavica, vol. 115, No. 2, Feb. 1, 2007, pp. 93-100.
European Search Report Issued by the European Patent Office for Application No. EP 16181339.9, dated Jan. 2, 2017, 3 pages.
Foussias, G., et al. "Negative Symptoms in Schizophrenia: Avolition and Occam's Razor", Schizophrenia Bulletin, vol. 36, No. 2, Jul. 21, 2008, pp. 359-369.
Takasu et al., Today's Therapy 2002, vol. 44, pp. 609-612.
Takahashi et al.,"Antipsychotic reverse abnormal EEG complexity in drug-naïve schizophrenia: A multiscale entropy analysis", NeuroImage, (2010), vol. 51, pp. 173-182.
Cohrs, "Sleep Disturbances in Patients with Schizophrenia", CNS Drugs, (2008), vol. 22, No. 11, pp. 939-962.
Ishihara et al., Japanese Journal of Neuropsychopharmacology, (2002), vol. 22, No. 1, pp. 23-30.

\* cited by examiner

METHODS OF USE OF CYCLIC AMIDE DERIVATIVES TO TREAT SCHIZOPHRENIA

CROSS-REFERENCE TO RELATED APPLICATIONS

The present application is a U.S. National Stage of International Application No. PCT/US11/44697, filed Jul. 20, 2011, which claims priority to U.S. Provisional Application No. 61/366,075, filed Jul. 20, 2010, the contents of which are hereby incorporated by reference in their entirety.

BACKGROUND

The mental disorder schizophrenia dramatically affects the health and well-being of individuals suffering from it. Individuals with schizophrenia can suffer from a myriad of symptoms and may require significant custodial care and continuous drug and/or behavior therapy, leading to substantial social and economic costs, even in the absence of hospitalization or institutionalization.

The symptoms of schizophrenia are divided into two broad classes: positive symptoms and negative symptoms.

Positive symptoms generally involve the experience of something in consciousness that should not normally be present. For example, hallucinations and delusions represent perceptions or beliefs that should not normally be experienced. In addition to hallucinations and delusions, patients with schizophrenia frequently have marked disturbances in the logical process of their thoughts. Specifically, psychotic thought processes are characteristically loose, disorganized, illogical, or bizarre. These disturbances in thought process frequently produce observable patterns of behavior that are also disorganized and bizarre. The severe disturbances of thought content and process that comprise the positive symptoms often are the most recognizable and striking features of schizophrenia.

In addition to positive symptoms, patients with schizophrenia have been noted to exhibit major deficits in motivation and spontaneity. These symptoms are referred to as negative symptoms.

While positive symptoms represent the presence of something not normally experienced, negative symptoms reflect the absence of thoughts and behaviors that would otherwise be expected and thus reflect a decrease or loss of normal function or the loss or absence of normal behaviors. Negative symptoms of schizophrenia include, for example, flat or blunted affect, concrete thoughts, anhedonia (the inability to experience pleasure), poor motivation, spontaneity, and initiative. Inflexibility or rigidity of thought represents impairment in the ability to think abstractly. Blunting of affect refers to a general reduction in the ability to express emotion. Motivational failure and inability to initiate activities represent an important source of long-term disability in schizophrenia. Anhedonia reflects a deficit in the ability to experience pleasure and to react appropriately to pleasurable situations.

Positive symptoms such as hallucinations are responsible for much of the acute distress associated with schizophrenia. Negative symptoms appear to be responsible for much of the chronic and long-term disability associated with the disorder. Current treatments for schizophrenia have shown limited benefit in the treatment of negative symptoms.

Negative symptoms of schizophrenia can be further subdivided into primary and secondary negative symptoms. Primary negative symptoms do not include symptoms that are better accounted for by medication side-effects, post-psychotic depression or demoralization. Rather, examples of primary negative symptoms include: affective flattening (for example emotional immobility, unresponsiveness, poor eye contact, and limited body movement); alogia (this is where the patient exhibits poverty of speech and usually manifests itself by the patient making brief replies during conversation); avolition (the inability to initiate and persist in goal-directed activities); anhedonia (loss of interest or pleasure); dysphoric mood (depression, anxiety and anger); disturbances in sleep pattern (sleeping during the day, restlessness/night-time activity); abnormal psychomotor activity (pacing, rocking, apathetic immobility); and lack of insight.

Secondary negative symptoms, some of which occur in association with positive symptoms and/or medication side-effects, include for example, movement disorders such as extrapyramidal symptoms, akathisia and tardive dyskinesia and demoralization.

There remains a need to identify medicaments and methods for use in the treatment of negative symptoms of schizophrenia, and furthermore, compositions and methods of treatment which improve on the efficacy of existing therapies.

DETAILED DESCRIPTION OF THE INVENTION

The sigma receptor/binding sites of the brain are important target for the development of antipsychotic drugs that are free from the side effects of traditional antipsychotic drugs, or have reduced side effects of traditional antipsychotic drugs having antagonistic activity on the dopamine D2 receptor (see, E.g., J. M. Walker et al., Pharmacological Reviews, 42:355-402, 1990).

The sigma 1 binding site was characterized to have high affinity for haloperidol, di-o-tolylguanidine (DTG) and (+)-benzomorphanes such as (+)-pentazocine. The sigma 2 binding site is characterized to have high affinity for haloperidol and DTG, but have low affinity for (+)-benzomorphane.

Sigma 1 ligands may act on the gastrointestinal tract. The sigma 1 site may mediate suppression to muscarine-like acetylcholine receptor/phosphoinositide response by the sigma ligands. The sigma 1 binding site is present not only in brains, but on spleen cells (Y. Lin et al., J. Neuroimmunol., 58:143-154, 1995), and such sigma ligands may suppress the immune system (H. H. Garza et al., J. Immunol., 151:4672-4680, 1993).

The sigma 2 binding site is abundant in livers (A. E. Bruce et al., Neurosci. Abstr., 16:370, 1990), kidneys (W. D. Bowen et al., Soc. Neurosci. Abstr., 18:456), and heart (M. Dumont and S. Lemaire, Eur. J. Pharmacol., 209:245, 248, 1991). The sigma 2 binding site in brain exists in the hypothalamus, cerebellum, pons medulla and medulla oblongata. In hippocampus, frontal lobe and occipital lobe in rat brains, it exists more abundantly than the sigma 1 binding site. In hippocampal synaptosomes of guinea pig, there is a sigma 2 binding site that is selectively labeled with [$^3$H] BIMU (D. W. Bonhaus et al., J. Pharmacol. Exp. Ther., 267:961-970, 1993). The relationship between the sigma 2 binding site and cortex as well as limbic system supports the usefulness of compounds used for treatment of mental diseases (D. C. Mash and C. P. Zabetian, Synapse, 12:195-205, 1992). It has been believed that the sigma 2 binding site is involved in motility functions, especially dystonia; however, no evidence demonstrating such an action has been found in primate models of functional disorders of extrapyramidal tract (L. T. Meltzer et al., Neuropharmacology, 31:961-967, 1992).

Haloperidol, a clinically effective dopaminergic antipsychotic agent, shows high affinity for both sigma subtypes 1 and 2. However, a reduced metabolite of haloperidol that acts on the central nervous system has higher affinity and selectivity for the sigma 2 receptor than dopamine D2, as compared to haloperidol (J. C. Jaen. et al., J. Med. Chem., 36:3929-3936, 1993).

U.S. Pat. No. 7,166,617, incorporated herein by reference in its entirety, discloses cyclic amide derivatives having high affinity for the sigma 2 binding site. Certain compounds disclosed in this patent also have high affinity for the sigma ligand binding site and low inhibition constant $K_i$ for sigma 1 and/or sigma 2, as well as selective binding profiles completely different from those of conventional known compounds. Such compounds may be useful for treatment of diseases that can be therapeutically and/or preventively treated by the nerve control function of the sigma ligands. However, the properties and characteristics of specific derivatives were not disclosed in U.S. Pat. No. 7,166,617.

In the present invention, compounds of formula I have been shown to have properties useful to treat schizophrenia and/or one or more symptoms of schizophrenia. In an aspect, compounds of formula I have been shown to be useful to treat one or more negative symptoms of schizophrenia. The invention therefore provides methods and compositions for treating various aspects of schizophrenia.

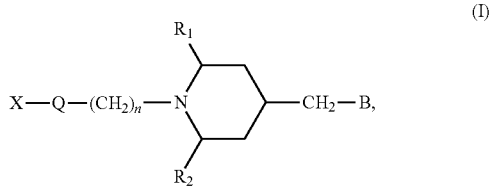

(I)

As used herein, the term "schizophrenia" covers the full spectrum of schizophrenic disorders known to the skilled person. These include, but are not limited to, the following: catatonic, disorganized, paranoid, residual and undifferentiated schizophrenia; schizophreniform disorder and schizoaffective disorder.

The term "receptor", as used herein, means a membrane-binding type receptor, as well as other binding sites. For example, the existence of at least two sigma receptor subtypes is known, i.e., sigma 1 and sigma 2, and classification of sigma binding sites has been proposed (R. Quirion et al., TiPS, 13:85-86, 1992).

The term "subject" refers to any animal, including mammals, such as, but not limited to, humans, mice, rats, other rodents, rabbits, dogs, cats, pigs, cattle, sheep, horses, or primates.

The term "treating" (and corresponding terms "treat" and "treatment") includes palliative, restorative, and preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of, or entirely eliminates a condition in a subject. Treating can be done with a therapeutically effective amount of compound, salt or composition that elicits the biological or medicinal response of a tissue, system or subject that is being sought by an individual such as a researcher, doctor, veterinarian, or clinician.

"PANSS" refers to the Positive and Negative Syndrome Scale.

"BACS" refers to the Brief Assessment of Cognition in Schizophrenia test.

"HAMD" refers to the Hamilton Depression Rating Scale.

"HAMA" refers to the Hamilton Anxiety Scale.

"ADAS COG" refers to the Alzheimer's Disease Assessment Seale—cognitive subscale and test.

"MADRS" refers to the Montgomery-Asberg Depression Rating Scale.

"PSQI" refers to the Pittsburgh Sleep Quality Index.

In one aspect of the present invention, compounds of formula I have been shown to have properties useful to treat schizophrenia and/or one or more symptoms of schizophrenia. In an aspect, compounds of formula I are useful to treat one or more negative symptoms of schizophrenia. In another aspect, compounds of formula I are useful to treat one or more negative symptoms of schizophrenia while not affecting one or more positive symptoms of schizophrenia. In another aspect, compounds of formula I are useful to treat one or more negative symptoms of schizophrenia while also treating one or more positive symptoms of schizophrenia. In another aspect, compounds of formula I are useful to treat one or more negative symptoms of schizophrenia while also treating one or more general symptoms of schizophrenia. In yet another aspect, compounds of formula I are useful to treat one or more positive symptoms of schizophrenia.

In another aspect, compounds of formula I are useful for augmenting treatment of schizophrenia in a subject presently receiving one or more compounds for the treatment of schizophrenia. In yet another aspect, compounds of formula I are useful for treating schizophrenia in combination with one or more additional antipsychotic compounds. In still another aspect, compounds of formula I are useful for treating schizophrenia in combination with one or more additional antipsychotic compounds, by decreasing the therapeutically effective dosage of the one or more antipsychotic compounds. In one aspect, compounds of formula I are useful for treating schizophrenia in combination with one or more additional antipsychotic compounds by decreasing the therapeutically effective dosage of the one or more antipsychotic compounds, wherein the dosage of the compound of formula I is also decreased.

In an aspect, compounds of formula I are useful for augmenting treatment of schizophrenia in a subject presently receiving one or more compounds for the treatment of schizophrenia by treating one or more negative symptoms of schizophrenia. In an embodiment, compounds of formula I are useful for treating schizophrenia in combination with one or more additional antipsychotic compounds, by improving at least one aspect and/or parameter of sleep in the subject.

In an embodiment, a compound of formula I includes the compound set forth in formula II:

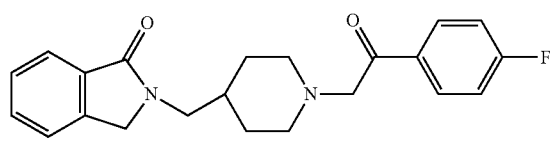

(II)

2-[[1-[2-(4-Fluorophenyl)-2-oxoethyl]piperidin-4-yl]methyl]isoindolin-1-one.

In another embodiment, a compound of formula I is the compound set forth in formula III:

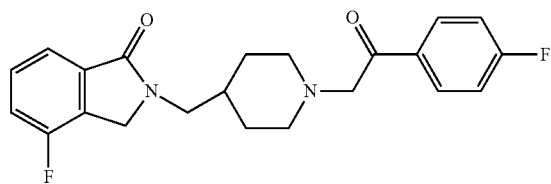

(III)

In one embodiment of the invention, the compound of formula III has properties and/or activity similar to a compound of formula II.

In an aspect, compounds of formula I disclosed herein have a receptor binding profile demonstrating preferential binding for sigma 2 receptors, 5-$HT_{2A}$ receptors, and $\alpha_1$ adrenergic receptors. In another aspect, compounds of formula I have a receptor binding profile comprising preferential affinity for sigma 2 receptors, while demonstrating little or no affinity for sigma 1 receptors. In yet another aspect, compounds of formula I have a receptor binding profile comprising preferential affinity for sigma 2 receptors than for sigma 1 receptors. However, it will be understood that certain compounds of formula I may not have a preferential binding for the same panel of receptors, and in some instances, may demonstrate preferential binding for one or more different receptors, including fewer than all of the sigma 2, 5-$HT_{2A}$, and $\alpha_1$ adrenergic receptors. In another aspect, compounds disclosed herein may have little or no affinity for dopaminergic, muscarinic, cholinergic or histaminergic receptors, and may have varying affinities for any combinations of those receptors. In one embodiment, a compound of formula II has little or no affinity for dopaminergic, muscarinic, cholinergic or histaminergic receptors.

In an aspect of the invention, a compound of formula I may have a receptor binding profile with a $K_i$ value of less than 5 nmol/L, less than 10 nmol/L for, less than 15 nmol/L, less than 20 nmol/L, less than 25 nmol/L, or less than 50 nmol/L for 5-$HT_2$, a $K_i$ value of less than 10 nmol/L, less than 15 nmol/L, less than 20 nmol/L, less than 25 nmol/L, or less than 30 nmol/L for $\alpha_1$ adrenergic receptors; and a $K_i$ value of less than 5 nmol/L, less than 10 nmol/L, less than 15 nmol/L, less than 20 nmol/L, and less than 25 nmol/L for the sigma 2 receptor, or any combination thereof. As will be understood by the skilled artisan, there may be variation in binding affinities for a compound of formula I when assayed against the same receptor from a different organism or species.

In an embodiment, a method is provided for treating schizophrenia in a subject comprising administering to a subject in need thereof a therapeutically effective amount of a compound of the formula (I) or a pharmaceutically acceptable salt, hydrate, or solvate thereof, wherein X represents an alkyl group, a cycloalkyl-substituted alkyl group, an aryl-substituted alkyl group, an aryl-substituted alkenyl group, an aryl-substituted alkynyl group, a monocyclic or polycyclic cycloalkyl group which may be substituted with an alkyl group, an aryl group, a heterocyclic group, or a substituted or unsubstituted amino group; Q represents a group represented by —CO—, —O—, —S—, —CH(OR₇)—, —C(=CH₂)— or —C(=NR₈)— wherein R₇ represents a hydrogen atom, an alkyl group, a hydroxyalkyl group, or an acyl group, and R₈ represents a hydroxyl group, an alkoxyl group, an aralkyloxy group, an acyloxy group, an acylamino group, or an alkoxycarbonyl amino group; n represents an integer of from 0 to 5; R₁ and R₂ each independently represent a hydrogen atom or an alkyl group.

In formula I, B represents the following groups:

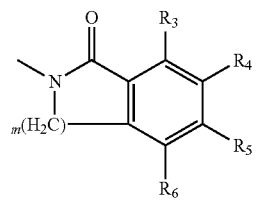

wherein R₃, R₄, R₅ and R₆ each independently represent a substituent selected from the group consisting of a hydrogen atom, a halogen atom, a nitro group, an alkyl group, a halogenated alkyl group, a hydroxyl group, an alkoxyl group, a halogenated alkoxyl group, and a cyano group; and m represents 1 or 2.

In an aspect, a compound of formula I does not demonstrate cytochrome P450 2D6 ("2D6") inhibitory and/or modulatory activity. In another aspect, a compound of formula I demonstrates minimal 2D6 inhibitory and/or modulatory activity, such that the compound is still useful in that it does not significantly decrease the effectiveness of the intended treatment.

Negative, Positive, General and Associated Symptoms of Schizophrenia

In one embodiment, a method is provided for treating at least one negative symptom of schizophrenia in a subject comprising administering to a subject in need thereof a therapeutically effective amount of a compound of the formula (I) or a pharmaceutically acceptable salt, as set forth above. In one embodiment, a method is provided wherein the compound is the compound set forth in formula II. In another embodiment, a method is provided wherein the compound is the compound set forth in formula III.

In an embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated. In an embodiment, at least one primary negative symptom is treated. In another embodiment, at least one secondary negative symptom is treated. In an embodiment, at least one disorder of sleep is treated. In another embodiment, at least one aspect or parameter of sleep is improved in a patient. In an embodiment, sleep is improved in a schizophrenic patient.

In an aspect, the disruption of at least one disorder or parameter of sleep is associated with schizophrenia. In an embodiment, the disruption of the at least one disorder or parameter of sleep is a negative symptom of schizophrenia. In another embodiment, the disruption of the at least one disorder or parameter of sleep is neither a positive nor a negative symptom of schizophrenia, but rather, is merely associated with the schizophrenia. The present disclosure provides for treatment of at least one disorder or parameter of sleep regardless of how the disorder or affected parameter of sleep arises.

In an embodiment, sleep is improved in a patient who does not have schizophrenia. In an aspect, at least one disorder or parameter of sleep is treated and/or improved. In an aspect, a method is provided for improving at least one aspect of sleep, comprising administering to a subject in need thereof a therapeutically effective amount of a compound of the formula (I) or a pharmaceutically acceptable salt, as set forth above. Various aspects of sleep may be treated, including, but not limited to, sleep onset latency, latency to persistent sleep, and the distribution of slow wave sleep across the sleep period time, or one or more segments of sleep period time. In an aspect, total sleep time is decreased. In an aspect, sleep efficiency index (SEI) is decreased by 2.4%. In an aspect, the duration of wake after sleep onset (WASO) is increased. In an aspect, slow wave sleep (SWS) is increased in the first third of sleep period time (SPT1). In an aspect, SWS is decreased in the last third of SPT (SPT3).

In an embodiment, a method is provided for treating or improving cognition, comprising administering to a subject in need thereof a therapeutically effective amount of a compound of the formula (I) or a pharmaceutically acceptable salt, as set forth herein. As will be understood based on the disclosure herein, modification of sleep parameters can improve cognition. By way of a non-limiting example, improvement and/or an increase in SWS improves cognition. In an aspect, cognition in general is improved. In another aspect, one or more aspects of cognition are improved, including, among others, memory consolidation, executive functions, verbal memory, and verbal fluency.

In an embodiment, a method is provided for treating or improving at least one aspect or parameter of sleep, comprising administering to a subject in need thereof a therapeutically effective amount of a compound of the formula (I) or a pharmaceutically acceptable salt, as set forth above, wherein the subject is affected with schizophrenia. In an aspect, a disorder of sleep is treated.

Negative symptoms of schizophrenia include, but are not limited to, blunted affect (E.g., diminished emotional responsiveness as characterized by a reduction in facial expression, modulation of feelings, and communicative gestures), emotional withdrawal (E.g., lack of interest in, involvement with, and affective commitment to life's events), poor rapport (E.g., lack of interpersonal empathy, lack of openness in conversation, lack of sense of closeness or interest, interpersonal distancing and reduced verbal and nonverbal communication), passive/apathetic social withdrawal (E.g., diminished interest and initiative in social interactions due to passivity, apathy, anergy, or avolition; reduced interpersonal involvement and neglect of activities of daily living), difficulty in abstract thinking (E.g., impairment in the use of the abstract-symbolic mode of thinking, as evidenced by difficulty in classification, forming generalizations, and proceeding beyond concrete or egocentric thinking in problem-solving tasks), lack of spontaneity and flow of conversation (E.g., Reduction in the normal flow of communication associated with apathy, avolition, defensiveness, or cognitive deficit, diminished fluidity and productivity of the verbal-interactional process), stereotyped thinking (E.g., decreased fluidity, spontaneity, and flexibility of thinking, as evidenced in rigid, repetitious, or barren thought content).

Other negative symptoms and examples thereof can be found, for example, in the PANSS scale, an instrument used clinically to rate burden of disease in schizophrenia. The full PANSS scale can be found at www<dot>tepou<dot>co<dot>nz/file/information-programme/panss.pdf (accessed on Jun. 14, 2010).

In an embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated, further wherein at least one positive symptom of schizophrenia is not treated. In another embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated, further wherein at least one positive symptom of schizophrenia is also treated.

Positive symptoms of schizophrenia include, but are not limited to, delusions (unfounded, unrealistic, idiosyncratic beliefs), conceptual disorganization (E.g., Disorganized process of thinking characterized by disruption of goal-directed sequencing, e.g., circumstantiality, tangentiality, loose associations, non sequiturs, gross illogicality, or thought block), hallucinations (E.g., Verbal report or behavior indicating perceptions which are not generated by external stimuli and which may occur in the auditory visual, olfactory, or somatic realms), hyperactivity and excitement (E.g., accelerated motor behavior, heightened responsivity to stimuli, hypervigilance, or excessive mood lability), grandiosity (E.g., exaggerated self-opinion and unrealistic convictions of superiority, including delusions of extraordinary abilities, wealth, knowledge, fame, power, and moral righteousness), suspiciousness/persecution (E.g., unrealistic or exaggerated ideas of persecution, as reflected in guardedness, a distrustful attitude, suspicious hypervigilance, or frank delusions that others mean one harm), and hostility (E.g., verbal and nonverbal expressions of anger and resentment, including sarcasm, passive-aggressive behavior, verbal abuse, and assaultiveness). Other positive symptoms and examples thereof can be found, for example, in the PANSS scale, as referenced above.

In an embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated, further wherein a general symptom of schizophrenia is not treated. In an embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated, further wherein at least one general symptom of schizophrenia is treated.

General symptoms of schizophrenia include, but are not limited to, somatic concern (E.g., physical complaints or beliefs about bodily illness or malfunctions), anxiety (E.g., subjective experience of nervousness, worry, apprehension, or restlessness, ranging from excessive concern about the present or future to feelings of panic), guilt-feelings (E.g., sense of remorse or self-blame for real or imagined misdeeds in the past), tension (E.g., overt physical manifestations of fear, anxiety, and agitation, such as stiffness, tremor, profuse sweating, and restlessness), mannerisms and posturing (E.g., unnatural movements or posture as characterized by an awkward, stilted, disorganized, or bizarre appearance), depression (E.g., feelings of sadness, discouragement, helplessness, and pessimism), motor retardation (E.g., reduction in motor activity as reflected in slowing or lessening of movements and speech, diminished responsiveness to stimuli, and reduced body tone), uncooperativeness (E.g., active refusal to comply with the will of significant others, including the interviewer, hospital staff, or family, which may be associated with distrust, defensiveness, stubbornness, negativism, rejection of authority, hostility, or belligerence), unusual thought content (E.g., thinking characterized by strange, fantastic, or bizarre ideas, ranging from those which are remote or atypical to those which are distorted, illogical, and patently absurd), disorientation (E.g., lack of awareness of one's relationship to the milieu, including persons, place, and time, which may be due to confusion or withdrawal), poor attention (E.g., failure in focused alertness manifested by poor concentration, distractibility from internal and external stimuli, and difficulty in harnessing, sustaining, or shifting focus to new stimuli), lack of judgment and insight (E.g., impaired awareness or understanding of one's own psychiatric condition and life situation), disturbance of volition (E.g., disturbance in the willful initiation, sustenance, and control of one's thoughts, behavior, movements, and speech), poor impulse control (E.g., disordered regulation and control of action on inner urges resulting in sudden, unmodulated, arbitrary, or misdirected discharge of tension and emotions without concern about consequences), preoccupation (E.g., absorption with internally generated thoughts and feelings and with autistic experiences to the detriment of reality orientation and adaptive behavior), and active social avoidance (E.g., diminished social involvement associated with unwarranted fear, hostility, or distrust). Other general symptoms and examples thereof can be found, for example, in the PANSS scale, as referenced above. As will be understood by the skilled artisan, the PANSS scale can be used to identify and/or measure general, positive and negative symptoms of schizophrenia.

Dosage Forms and Amounts

For therapeutic administration according to the present invention, a compound of formula I may be employed in the form of its free base, but is preferably used in the form of a pharmaceutically acceptable salt, typically the hydrochloride salt.

Alternative salts of a compound of formula I with pharmaceutically acceptable acids may also be utilized in therapeutic administration, for example salts derived from the functional free base and acids including, but not limited to, palmitic acid, hydrobromic acid, phosphoric acid, acetic acid, fumaric acid, maleic acid, salicylic acid, citric acid, oxalic acid, lactic acid, malic acid, methanesulphonic acid and p-toluene sulphonic acid.

All solvates and all alternative physical forms of a compound of formula I or its pharmaceutically acceptable derivatives as described herein, including but not limited to alternative crystalline forms, amorphous forms and polymorphs, are also within the scope of this invention, and all references to a compound of formula I herein include all pharmaceutically acceptable salts, and all solvates and alternative physical forms thereof.

For therapeutic administration, a compound of formula I or a pharmaceutically acceptable salt thereof, for example, the compound of formula II, may be administered in pure form, but will preferably be formulated into any suitable pharmaceutically acceptable and effective composition which provides effective levels of the active ingredient in the body.

Preferred forms include, but are not limited to, depot formulations (E.g., crystalline, emulsion), depot formulations suitable for intra-muscular or sub-dermal injection, controlled release forms, including controlled release tablets, transdermal systems (E.g., patch), buccal forms (E.g., film, tablet), effervescent tablets, and sub-dermal trochy. In an embodiment, a depot formulation comprises a palmitate salt of a compound of formula I.

In an aspect, a method of administering a compound of formula I may include titration of the compound up to a predetermined level. In one embodiment, a compound is used at a specified level (E.g., 2 mg b.i.d., 4 mg b.i.d., 8 mg b.i.d., 16 mg b.i.d.). In one embodiment, the compound is titrated up to a predetermined dosage (E.g., titration up to 16 mg b.i.d., 32 mg b.i.d., 64 mg b.i.d., etc.).

Administration of a compound for any purpose as described herein, in any form or combination described herein, may include administering the compound of formula I or a pharmaceutically acceptable salt thereof at a dose of between 10 ng-1 g, 100 ng-750 mg, 500 ng-500 mg, 10 µg-200 mg, 15 µg-190 mg, 25 µg-180 mg, 50 µg-170 mg, 75 µg-160 mg, 100 µg-150 mg, 250 µg-140 mg, 400 µg-130 mg, between 500 µg-128 mg, 600 µg-100 mg, 750 µg-75 mg, 900 µg-50 mg, or at a dose between 1 mg-64 mg. The treatment of schizophrenia may include administering the compound of formula I or a pharmaceutically acceptable salt thereof at a dose of <1 g, <500 mg, <200 mg, <150 mg, <100 mg, <50 mg, <40 mg, <30 mg, <20 mg, <10 mg, <9 mg, <8 mg, <7 mg, <6 mg, <5 mg, <4 mg, <3 mg, <2 mg, <1 mg, <0.5 mg, <0.25 mg, <0.1 mg, <0.05 mg, or <0.01 mg, <0.005 mg, or <0.001 mg. The dose may be administered as a weekly dose, a dose every other day, a single daily dose, twice daily, three times daily, four times daily, five times daily, or more frequently. In an embodiment, the compound of formula I or a pharmaceutically acceptable salt thereof is administered at a dose of between 8 mg-32 mg twice daily.

In an embodiment, a compound of formula I or a pharmaceutically acceptable salt thereof is administered independently of any other medication.

In an embodiment, a compound of formula I or a pharmaceutically acceptable salt thereof is administered to a subject that is an efficient 2D6 metabolizer. As will be understood by one of skill in the art, an efficient 2D6 metabolizer is a subject having average or greater than average 2D6 metabolic activity.

Co-Administration of Compounds

In another embodiment, a compound of formula I or a pharmaceutically acceptable salt thereof is administered in conjunction with one or more other medications. Such other medications may be administered or co-administered in forms and dosages as known in the art, or in the alternative, as has been described above for administration of compounds of formula I.

A compound of formula I, for example, the compound set forth in formula II, or a pharmaceutically acceptable salt of either, may advantageously be administered in combination with at least one neuroleptic agent (E.g., a typical or an atypical antipsychotic agent) to provide improved treatment of any combination of negative symptoms of schizophrenia, positive symptoms of schizophrenia, general symptoms of schizophrenia, or the treatment of schizophrenia itself. The combinations, uses and methods of treatment of the invention may also provide advantages in treatment of patients who fail to respond adequately or who are resistant to other known treatments.

In an embodiment, a compound of formula I may be administered to a patient already undergoing treatment with at least one neuroleptic agent (E.g., a typical or an atypical antipsychotic agent), to provide improved treatment of any combination of negative symptoms of schizophrenia, positive symptoms of schizophrenia, general symptoms of schizophrenia, or the treatment of schizophrenia itself.

Atypical antipsychotics include, but are not limited to, olanzapine, clozapine, risperidone, paliperidone, aripiprazole, quetiapine, iloperidone, ziprasidone, asenapine, lurasidone, sertindole, amisulpride, clotiapine, mosapramine perospirone, sulpiride, and zotepine. Typical antipsychotics include, but are not limited to, haloperidol, benperidol, loxapine, molindone, pimozide, thioridazine, mesoridazine, thiothixene, chlorprothixene, fluphenazine, trifluoperazine, chlorpromazine, perphenazine, prochlorperazine, droperidol, and zuclopenthixol.

In an aspect, a compound that is co-administered with a compound of formula I does not demonstrate any 2D6 inhibitory and/or modulatory activity. In another aspect, a compound that is co-administered with a compound of formula I demonstrates minimal 2D6 inhibitory and/or modulatory activity, such that the compound is still useful in that it does not significantly decrease the effectiveness of the intended treatment.

Augmentation of Treatment of Symptoms and Schizophrenia

In an embodiment, a compound of formula I may be administered to a patient in conjunction with at least one neuroleptic agent, or to a patient already undergoing treatment with at least one neuroleptic agent, to provide improved treatment of any combination of negative symptoms of schizophrenia, positive symptoms of schizophrenia, general symptoms of schizophrenia, or the treatment of schizophrenia itself. In an embodiment, the administration of a compound of formula I lowers the concentration of the neuroleptic agent required to achieve a therapeutically effective amount of the neuroleptic agent. In an aspect, the compound of formula I provides a synergistic effect to the neuroleptic agent.

In an embodiment, a compound of formula I may be administered to a patient in conjunction with at least one neuroleptic agent, or to a patient already undergoing treatment with at least one neuroleptic agent, wherein the neuroleptic agent does not prolong the QT interval. Such neuroleptic agents include, but are not limited to, risperidone, quetiapine, aripiprazole, and olanzapine, and pharmaceutically acceptable salts thereof; including, but not limited to, palmitate salts. In an aspect, a compound of formula I, such as the compound set forth in formula II, will be paired with one or more antipsychotic compounds having a low QT prolongation liability. It will be clear to the skilled artisan how to select, identify and/or characterize the QT prolongation liability of an antipsychotic, particularly in view of the guidance set forth herein.

In an embodiment, a compound of formula I may be administered to a patient in conjunction with at least one neuroleptic agent, or to a patient already undergoing treatment with at least one neuroleptic agent, wherein the administration of the compound of formula I further augments the treatment of at least one negative symptom of schizophrenia. In another embodiment, a compound of formula I may be administered to a patient in conjunction with at least one neuroleptic agent, or to a patient already undergoing treatment with at least one neuroleptic agent, wherein the administration of the compound of formula I further augments the treatment of any combination of at least one negative symptom of schizophrenia, at least one positive symptom of schizophrenia, at least one general symptom of schizophrenia, or the schizophrenia itself.

In an embodiment, a method is provided for treating at least one negative symptom of schizophrenia in a subject comprising administering to a subject in need thereof a therapeutically effective amount of a compound of the formula (I) or a pharmaceutically acceptable salt, as set forth above, wherein the at least one negative symptom is treated, further wherein schizophrenia-related cognition is improved. Cognitive skills include, but are not limited to, motor speed, verbal memory, and verbal fluency. Improvement of cognition is described in greater detail elsewhere herein.

EXPERIMENTAL EXAMPLES

Example 1: Clinical Study of CYR-101

A study was conducted using the compound of formula II, to examine the efficacy on schizophrenia and treatment of symptoms of schizophrenia. The study was a multi-center, inpatient and ambulatory, phase 2, double-blind, randomized, placebo-controlled proof of concept study of the compound of formula II in patients with DSM-IV schizophrenia. The study used 21 centers across three different countries.

The study was designed to test the therapeutic efficacy of the compound of formula II on all dimensions of schizophrenic disease (E.g., positive, negative, and general symptoms, cognition, sleep, mood and anxiety). The study also examined the safety of the administered doses of the compound of formula II (also referred to herein as CYR-101), including heart repolarization (i.e., QT interval), weight change, adverse events, prolactin, and extrapyramidal symptoms).

The study was conducted for a time period of three months. This time period was sufficient to allow for the compound to demonstrate full therapeutic potential, particularly with respect to cognitive parameters.

The objectives of the study included the following:
1. Evaluate the efficacy versus placebo of CYR-101 on global PANSS score and sub-scores after one month (28 days+/− 2 days) of treatment
2. Test whether the administered dose of CYR-101 will demonstrate significantly greater efficacy as assessed by PANSS total score and sub-scores after three months (84 days+/− 2 days) of treatment
3. Evaluate the efficacy versus placebo of CYR-101 as assessed by the CGI-S after one and three months of treatment
4. Evaluate subjective efficacy in patients of CYR-101 versus placebo as assessed by the Drug Attitude Inventory-10 (DAI-10) after one and three months of treatment
5. Evaluate subjective sleep quality as assessed by Pittsburgh Sleep Quality Index (PSQI) after three month of treatment
6. Explore the efficacy versus placebo of CYR-101 on cognitive function as measured by BACS (Brief Assessment of Cognition in Schizophrenia) scale after one and three months of treatment
7. Evaluate the efficacy versus placebo of CYR-101 in depressive symptoms as measure by the Montgomery-Asberg Depression Rating Scale (MADRS) total score after one month of treatment 8. Evaluate the efficacy versus placebo of CYR-101 in anxiety as measured by the Hamilton Anxiety Scale (HAMA) total score after one month of treatment
9. Assess cardio-vascular safety (particularly ventricular repolarisation as assessed by QT/QTc interval measurements) of CYR-101 compared with placebo
10. Assess the global safety and tolerability of CYR-101 compared with placebo
11. Determine the pharmacokinetics of CYR-101 in schizophrenic patients CYR-101 8 mg oral sustained release (SR) tablet, oral administration of 1, 2, or 4 tablets (8, 16 or 32 mg of CYR-101) was administered twice daily in fed condition. During the dose adjustment period, CYR-101 was administered orally, twice a day in the morning and in the evening, at the daily dose of 16 mg for two days, then titrated up every two days to 32 mg and 64 mg respectively. During the fixed-dose period, the optimal adjusted dose evaluated for each patient or the maximum daily dose of 64 mg of CYR-101 was administered. In one aspect of the study, the dosage of compound was titrated up to 32 mg b.i.d.

During the lead-in period, oral administration of 1 placebo SR tablet was conducted twice a day for 3 days. During the dose adjustment and fixed-dose periods, oral administration of 1, 2, or 4 placebo SR tablets was used twice daily as performed for the test product.

The resulting data was analyzed one of three ways: 1.) Safety set; 2.) Full analysis set, with each patient having at least one PANSS evaluation after treatment initiation included in the efficacy analysis. The LOCF method is used; and 3.) Per protocol set, where for certain analyses, all patients having completed three months of treatment are included. ANCOVA followed by a contrast analysis at each time point were applied and in some cases, a non-parametric Wilcoxon test was used.

The criteria used for evaluation were as follows:
1. Primary: PANSS total score and sub-scores, after one month of treatment
2. Secondary: PANSS total score and sub-scores after three months of treatment, CGI-S score, DAI-10 score, PSQI score, BACS tests scores, MADRS total score, and HAMA total score, Readiness of Discharge Questionnaire (RDQ).
3. Exploratory: In a sub-group of patients, polysomnographic sleep continuity and sleep architecture parameters.
4. Safety: 12-lead ECG, adverse event (AE) recording, vital signs, physical examination, weight and waist circumference, safety lab tests, evaluation of extra-pyramidal symptoms (measured by Simpson and Angus scale), and prolactin levels.
5. Pharmacokinetics: CYR-101, BFB-520, and BFB-999 levels in plasma.

The statistical methods used were as follows:
1. Primary efficacy variable: Analysis of Covariance (ANCOVA) with treatment and centre as fixed effects and baseline value as eovariate, after one month of treatment, on change from baseline for PANSS total score and sub-scores on the Full Analysis Set (FAS).
2. Secondary efficacy variables: Same method for the PANSS total and sub-scores at three months of treatment, BACS, DAI-10, MADRS, HAMA, and PSQI on the Full Analysis Set (FAS). Last Observation Carried Forward (LOCF) procedure used for missing data imputation. Analysis of variance (ANOVA) for the Readiness for Discharge Questionnaire (RDQ) at 14 days. Wilcoxon rank sum test for CGI-S. Descriptive statistics and graphical presentation on changes from baseline on FAS. Efficacy analyses (ANCOVA) additionally performed on the Per Protocol Set. Supportive exploratory analysis on PANSS using longitudinal, likelihood-based, mixed-effect model on FAS without missing data imputation. On a subtest of patients, polysomnographic (PSG) recording parameters analyzed using descriptive statistics and ANCOVA on changes from baseline.
3. Safety: Descriptive statistics on the safety set for extent of exposure, adverse events recording, safety lab tests, 12-lead ECG parameters, vital signs, and physical examination, weight and waist circumference, extra-pyramidal symptoms, prolactin levels.

Results Summary

The results showed no significant difference between CYR-101 and placebo groups with respect to the emergence or worsening of extrapyramidal symptoms. There were three statistically significant adverse events (SAE), two of which were in the placebo group. The one SAE in the active treatment group was unlikely related to CYR-101 based on the patient history.

Improvement of negative symptoms was observed immediately, and continued through the course of treatment. This effect of the compound was surprising. Positive symptoms did not improve until after the first four weeks of treatment. Moreover, improvement in both positive and negative symptoms continued for more than twelve weeks. This is also surprising, as other antipsychotics typically only show improvement for six weeks.

Further, it is noted that CYR-101 has a positive effect on cognition in schizophrenic patients. Cognition was shown to improve quickly upon beginning treatment of patients with CYR-101. Cognitive performances assessed by the mean of the BACS show on the FAS, no differences between the placebo group and the CYR-101 group, except for the Token motor task. On the PPC at D84, descriptive data show a slight difference in favor of CYR-101 group in comparison to the placebo group for the Token motor task, list learning task and for verbal fluency, as well as for processing speed. These differences were not statistically significant. However, in comparison, it should be noted that most other antipsychotic treatments have a marked negative effect on cognition.

An increase in the QT interval was observed after CYR-101 was administered at doses up to 32 mg b.i.d. However, the observed increase remained stable over time and did not cross clinically acceptable limits (E.g., 10-15 milliseconds or less).

In summary, CYR-101 induced surprising and unexpected immediate and sustained effects on negative symptoms and some cognitive functions disturbed in schizophrenic patients. CYR-101 has also some effects on positive symptoms but there is a need of a longer period of treatment to start to see a differentiation from placebo. All the above mentioned effects are accompanied by some improvements of mood, anxiety and sleep, making CYR-101 a desirable basis for therapy to treat schizophrenia and symptoms of schizophrenia with a minimum of side effects and an advantageous, immediate, and beneficial effect on negative symptoms and cognition.

Detailed Results

The change from baseline in PANSS total score after one month of treatment (at D28) is the primary criteria of efficacy. At D28, on the FAS, the PANSS total score, the PANSS general psychopathology sub-score and the PANSS positive sub-score, show a decrease in both groups with no treatment difference between placebo and CYR-101 groups.

At D28, on the PPC, the PANSS total score, the PANSS general psychopathology sub-score and the PANSS positive sub-score show a statistically significant decrease for both groups with no treatment difference between placebo and CYR-101 groups.

The FAS results of the PANSS negative sub-score at D28 demonstrate a favorable trend superiority of CYR-101 over placebo with a statistically significant decrease of −1.7, (p<0.05) and −1.9, (p<0.01), for placebo and CYR-001 respectively. The pattern shown in FAS analysis is confirmed on PPC results. The PANSS negative sub-score at D28 demonstrate a more favorable superiority of CYR-101 over placebo with a statistically significant decrease of −4.2, (p<0.0010) and −4.7, (p<0.0010), for placebo and CYR-001 respectively.

Similar to the results following one month of treatment, at D84 on the FAS the change from baseline in the PANSS total score, the PANSS general psychopathology sub-score and the PANSS positive sub-score showed no significant treatment difference between placebo and CYR-101 groups. In contrast to the result on the FAS, results on the PPC showed a favorable trend of CYR-101 over placebo with an obvious switch on D56 for the PANSS total score, on D70 for the PANSS general psychopathology sub-score and between D56 and D70 on the PANSS positive sub-score.

The FAS results of the PANSS negative sub-score at D84 demonstrate a favorable trend of CYR-101 over placebo with only CYR-101 demonstrating a statistically significant decrease with respect to placebo: a point estimate decrease of −1.2, (p=0.126) and −2.3, (p<0.01), for placebo and CYR-101 respectively.

This favorable trend of CYR-101 over placebo is strongly supported by the PPC analysis of the PANSS negative sub-score at D84. The decrease is statistically significant for both groups and more obvious for CYR-101 with an improvement of −3.4, (p=0.0077) and −5.8, (p<0.001), respectively for placebo and CYR-101. In addition, this superiority shows a nearly statistically significant (p=0.0581) treatment difference in favor of CYR-101.

The CGI-S score shows no significant difference between CYR-101 and placebo on the FAS at D28 and D84. On the PPC, from D56 until D84, there is a non significant but an interesting switch in favor of CYR-101 on the CGI-S mean difference score.

DAI-10 total score change from baseline to D28 and D84 show no statistically significant difference between the two groups, on the FAS and the PPC.

PSQI results indicate on the FAS that sleep quality was better for both groups at the end of the study. This improvement was greater in CYR-101 group (−4 points±4.9) in comparison to placebo group (−1.4 points±6.6). As for the FAS results, the PPC data indicate that sleep quality was better for both groups at the end of the study. This improvement was greater in CYR-101 group (−4.6 points±4.3) in comparison to placebo group (−1.2 points±6.2).

Cognitive performances assessed by the mean of the BACS show on the FAS, no differences between the placebo group and the CYR-101 group, except for the Token motor task. On the PPC at D84, descriptive data show a slight difference in favour of CYR-101 group in comparison to the placebo group for the Token motor task, list learning task and for verbal fluency. These differences were not statistically significant.

A reduction of the MADRS Total change score was observed on the FAS and PPC at D28 and D84 in both groups. These differences were not statistically significant.

At D28 and D84 on the FAS, the results show a slight HAMA total score reduction in both groups with a non statistically significant change from baseline. The time course pattern on the PPC is different as at D28, despite no statistically significant treatment difference between both groups, data show a significant reduction of −1.6, (p=0.1000) and −1.0, (p=0.2920), for placebo and CYR-101 respectively. At D84, there is a switch in favor of CYR-101. Both groups group showed a numerical reduction greater in CYR-101 group compared with the placebo group: −2.2, (p=0.1523) and −2.9, (p=0.0642).

Polysomnographic (PSG) recording data show that sleep maintenance parameters indicate no significant treatment effect. Contrasts revealed that, compared to placebo, CYR-101 decreased total sleep time (TST) by 13.7 min and sleep efficiency index (SEI) by 2.4% and increased duration of wake after sleep onset (WASO) by 26.6 min. These differences did not reach statistical significance.

Analysis of the stages distribution parameters indicate no significant treatment effect. Contrasts revealed that, compared to placebo, CYR-101 increased Total Time Awake (TTA), Slow Wave Sleep (SWS) and nonREM sleep (NREM) while it decreased Stage 1 (ST1), Stage 2 (ST2 in min) and REM sleep (REM). These differences did not reach statistical significance excepting for REMTST (p<0.05). Two significant treatment effects (p<0.05) appear on the distribution of slow wave sleep across the first and the last third of the sleep period time (SPT). Significant contrasts (p<0.05) revealed that, compared to placebo, CYR-101 increased SWS in the first third of SPT (SWS-SPT1) by 23.6% while it decreased it during the last third (SWS-SPT3) by 22.1%. REM sleep was found slightly increase by 1.4% in the first third of SPT (REM_SPT1) and slightly decreased thereafter (by 3.03% in SPT2 and in SPT3). These results were not statistically significant. Both non significant latencies contrasts results showed that SWS appeared sooner and REM sleep appeared later with CYR-101.

Example 2: Properties of CYR-101

U.S. Pat. No. 7,166,617, incorporated herein by reference in its entirety, illustrates the preferential binding of CYR-101 to the sigma 2 receptor site. The test compound of Example 1 of U.S. Pat. No. 7,166,617 is CYR-101. As illustrated in Table 3 in U.S. Pat. No. 7,166,617, CYR-101 has an affinity of 13 nM for the sigma 2 receptor. This data illustrates that CYR-101 demonstrates sigma 2-selective receptor binding. Furthermore, it is known that CYR-101 is a dual 5-HT2A/sigma 2 antagonist and is devoid of dopamine binding properties.

Example 3: Effect of CYR-101 on Sleep

A study of the effect of CYR-101 on sleep suggests that CYR-101 improves sleep in schizophrenic patients, and may be more generally useful for treatment of sleep disorders.

Polysomnographic recordings took place in a sub-group of patients. Sleep was recorded from 11:00 pm to 7:00 am on D-1 after a habituation night (baseline condition) and on D14. Analyses regarding sleep continuity, stage distribution, and stage profile parameters were exploratory. The treatment differences on each of these sleep parameters were analyzed using D14 values with ANOVAs and ANCOVAs with country and treatment as main effects and baseline as covariate.

Among the 33 patients who had performed a PSG recording at visit lead-in day-1, 19 received placebo and 14 received the study treatment. Among these, 7 patients experienced technical problem and/or insomnia during baseline and/or treatment night and were therefore excluded from the analysis. Finally, 20 patients were included in the analysis set of ANOVA and 19 patients were included in the analysis set of ANCOVA, and according to the SAP, only ANCOVA results were taken into account and are further discussed in the next sections.

Results of the ANCOVA performed on the sleep initiation parameters indicate no significant treatment effect. However, a trend of improvement can be observed on sleep onset latency as well as on latency to persistent sleep. Results of the ANCOVA performed on the sleep maintenance parameters indicate no significant treatment effect. Contrasts revealed that, compared to placebo, CYR-101 decreased total sleep time (TST) by 13.7 min and sleep efficiency index (SEI) by 2.4% and increased duration of wake after sleep onset (WASO) by 26.6 min. These differences did not reach statistical significance.

Results of the ANCOVA performed on the stages distribution parameters indicate no significant treatment effect. Contrasts revealed that, compared to placebo, CYR-101 increased Total Time Awake (TTA), Slow Wave Sleep (SWS) and nonREM sleep (NREM) while it decreased Stage 1 (ST1), Stage 2 (ST2 in min) and REM sleep (REM). These differences did not reach statistical significance excepting for REM-TST ($p<0.05$).

Results of the mixed model performed on the sleep profile parameters indicate two significant treatment effects ($p<0.05$) on the distribution of slow wave sleep across the first and the last third of the sleep period time (SPT). Significant contrasts ($p<0.05$) revealed that, compared to placebo, CYR-101 increased SWS in the first third of SPT (SWS-SPT1) by 23.6% while it decreased it during the last third (SWS-SPT3) by 22.1%. REM sleep was found slightly increase by 1.4% in the first third of SPT (REM_SPT1) and slightly decreased thereafter (by 3.03% in SPT2 and in SPT3) but these results were not statistically significant. Both non significant latencies contrasts results showed that SWS appeared sooner and REM sleep appeared later with CYR-101.

The results of the present study indicate that CYR-101 had no significant effect on sleep EEG parameters except for the slow wave sleep distribution. CYR-101 shifted the slow wave sleep distribution from the end to the beginning of the night: it significantly increased slow wave sleep in the first third of the night and decreased it in the last third of the night. Results also suggest that CYR-101 could have sleep promoting effects since it improved (but not significantly) sleep initiation parameters. It is important to note that these results were obtained in a parallel group design on a very small sample of patients (N=19) of which only 7 received CYR-101. Moreover, sleep EEG parameters in patients with schizophrenia have a high degree of variability (due to illness heterogeneity and/or concomitant medication). In this context, some of the differences observed in the present study could have reached statistical significance with a larger sample size.

Based on the disclosure herein, one of skill in the art will understand how to treat a sleep disorder or how to improve a parameter of sleep. Further, based on the disclosure herein, one of skill in the art will understand how to measure and/or evaluate effective treatment of a sleep disorder or improvement of a parameter of sleep. In a general sense, any enhancement to or improvement in the quality of sleep, or in the beneficial effect obtained from sleep, may be considered a treatment or an improvement.

The invention has been described herein by reference to certain preferred embodiments. However, as particular variations thereon will become apparent to those skilled in the art, based on the disclosure set forth herein, the invention is not to be considered as limited thereto. All patents, patent applications, and references cited anywhere is hereby incorporated by reference in their entirety.

The invention claimed is:

1. A method of treating or diminishing at least one negative symptom of schizophrenia in a human subject comprising administering to a human subject in need thereof a therapeutically effective amount of a compound of the formula (II) or a pharmaceutically acceptable salt, hydrate, or solvate thereof,

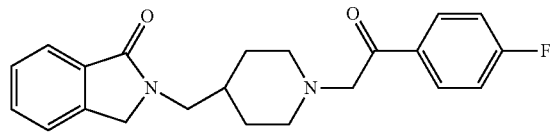

(II)

wherein said compound is administered at a dose of between 0.1 mg and 128 mg.

2. The method of claim 1, wherein the negative symptom is selected from the group consisting of blunted affect, emotional withdrawal, poor rapport, passive/apathetic social withdrawal, difficultly in abstract thinking, lack of spontaneity and flow of conversation, and stereotyped thinking.

3. The method of claim 2, wherein the negative symptom is selected from the group consisting of a primary negative symptom and a secondary negative symptom.

4. The method of claim 2, wherein a hydrochloride salt of said compound is administered.

5. The method of claim 2, wherein said compound is administered at a dose of between 1 mg and 64 mg.

6. The method of claim 5, wherein said compound is administered between once daily and four times daily.

7. The method of claim 6, wherein a hydrochloride salt of the compound is administered.

8. The method of claim 7, wherein a hydrate of the hydrochloride salt is administered.

9. The method of claim 2, wherein said compound is administered at a dose of between 8 mg and 32 mg.

10. The method of claim 9, wherein said compound is administered between once daily and four times daily.

11. The method of claim 2, wherein said compound is administered between once daily and four times daily.

12. The method of claim 2, wherein said compound is administered twice daily.

13. The method of claim 2, wherein said compound is administered between 8 mg and 32 mg twice daily.

14. The method of claim 1, wherein a hydrochloride salt of said compound is administered.

15. The method of claim 1, wherein said compound is administered at a dose of between 1 mg and 64 mg.

16. The method of claim 15, wherein said compound is administered between once daily and four times daily.

17. The method of claim 1, wherein said compound is administered at a dose of between 8 mg and 32 mg.

18. The method of claim 17, wherein said compound is administered between once daily and four times daily.

19. The method of claim 1, wherein said compound is administered between once daily and four times daily.

20. The method of claim 1, wherein said compound is administered twice daily.

21. The method of claim 1, wherein said compound is administered between 8 mg and 32 mg twice daily.

22. The method of claim 1, wherein the negative symptom is a primary negative symptom and said compound is administered at a dose of between 1 mg and 64 mg.

23. The method of claim 22, wherein a hydrochloride salt of the compound is administered.

24. The method of claim 23, wherein a hydrate of the hydrochloride salt is administered between once daily and four times daily.

25. The method of claim 24, wherein said primary negative symptom is selected from the group consisting of blunted affect, emotional withdrawal, poor rapport, passive/apathetic social withdrawal, difficultly in abstract thinking, lack of spontaneity and flow of conversation, and stereotyped thinking.

\* \* \* \* \*

UNITED STATES PATENT AND TRADEMARK OFFICE
CERTIFICATE OF CORRECTION

PATENT NO. : 9,732,059 B2 Page 1 of 1
APPLICATION NO. : 13/810772
DATED : August 15, 2017
INVENTOR(S) : Luthringer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 558 days.

Signed and Sealed this
Twenty-fifth Day of September, 2018

Andrei Iancu
*Director of the United States Patent and Trademark Office*